US012657712B2

(12) United States Patent
Sakuma et al.

(10) Patent No.: US 12,657,712 B2
(45) Date of Patent: Jun. 16, 2026

(54) INFORMATION PROCESSING SYSTEM, PROGRAM, AND INFORMATION PROCESSING METHOD

(71) Applicant: THE UNIVERSITY OF TOKYO, Tokyo (JP)

(72) Inventors: Ichiro Sakuma, Tokyo (JP); Naoki Tomii, Tokyo (JP); Keisuke Hori, Tokyo (JP)

(73) Assignee: THE UNIVERSITY OF TOKYO (JP)

( * ) Notice: Subject to any disclaimer, the term of this patent is extended or adjusted under 35 U.S.C. 154(b) by 256 days.

(21) Appl. No.: 18/715,271

(22) PCT Filed: Dec. 9, 2022

(86) PCT No.: PCT/JP2022/045402
§ 371 (c)(1),
(2) Date: May 31, 2024

(87) PCT Pub. No.: WO2023/106387
PCT Pub. Date: Jun. 15, 2023

(65) Prior Publication Data
US 2025/0037274 A1     Jan. 30, 2025

Related U.S. Application Data

(60) Provisional application No. 63/288,009, filed on Dec. 10, 2021.

(51) Int. Cl.
*G06T 7/00* (2017.01)
*G16H 30/20* (2018.01)

(52) U.S. Cl.
CPC ........... *G06T 7/0012* (2013.01); *G16H 30/20* (2018.01); *G06T 2207/30048* (2013.01)

(58) Field of Classification Search
CPC ........ G06T 7/0012; G06T 2207/30048; G16H 30/20; G16H 30/40; A61B 5/349
See application file for complete search history.

(56) References Cited

U.S. PATENT DOCUMENTS

| | | | |
|---|---|---|---|
| 2020/0037908 A1* | 2/2020 | Sakuma | A61B 5/339 |
| 2020/0113465 A1* | 4/2020 | Cohen | A61B 5/742 |

(Continued)

FOREIGN PATENT DOCUMENTS

| | | |
|---|---|---|
| JP | 2018-171194 A | 11/2018 |
| JP | 2020-62403 A | 4/2020 |

(Continued)

OTHER PUBLICATIONS

International Search Report of the International Searching Authority, issued in PCT/JP2022/045402, mailed Jan. 31, 2023; ISA/JP; (5 pages).

*Primary Examiner* — Utpal D Shah

(74) *Attorney, Agent, or Firm* — Harness, Dickey & Pierce, P.L.C.

(57) ABSTRACT

An information processing system is provided. This information processing system is equipped with an acquisition unit, a derivation unit, a detection unit and a generation unit. The acquisition unit acquires a first image sequence which expresses a change in membrane potential in biological tissue. The derivation unit derives a second image sequence which expresses a change in membrane potential by using a circulation variable on the basis of the first image sequence and a first derivation formula. The detection unit detects the position in the biological tissue at which the focal excitation wave is produced on the basis of the second image sequence and a first detection formula. The generation unit generates position information pertaining to the production position.

10 Claims, 13 Drawing Sheets

(56) References Cited

U.S. PATENT DOCUMENTS

| | | | | |
|---|---|---|---|---|
| 2022/0099775 A1* | 3/2022 | Li | .......................... | A61B 5/055 |
| 2022/0175315 A1* | 6/2022 | Tomii | ....................... | A61B 5/25 |
| 2022/0308148 A1* | 9/2022 | Katscher | ............. | A61B 5/0536 |

FOREIGN PATENT DOCUMENTS

| | | | |
|---|---|---|---|
| WO | 2018/180796 A1 | 10/2018 |
| WO | 2020/153468 A1 | 7/2020 |

* cited by examiner

FIG. 5

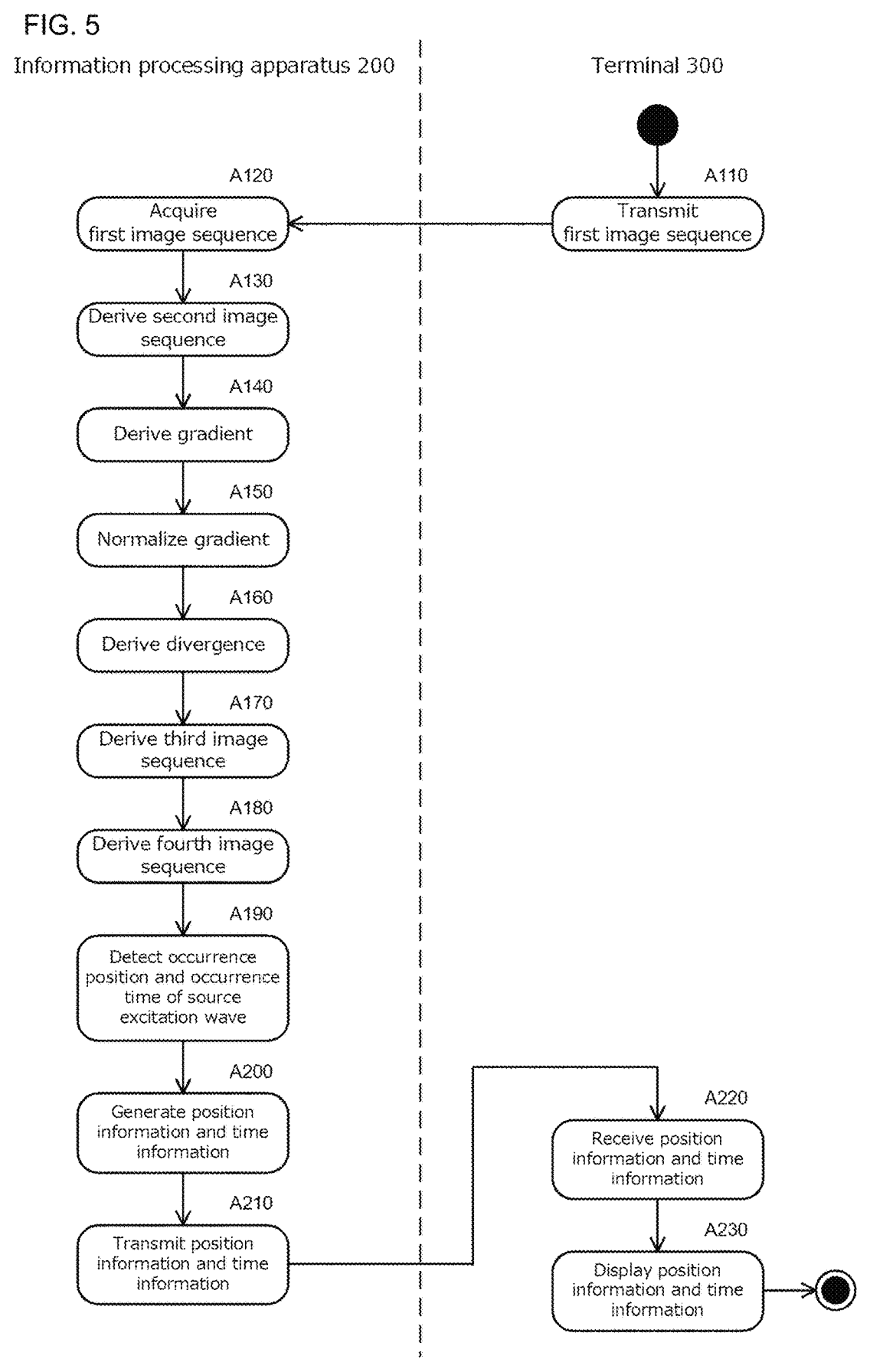

Information processing apparatus 200

Terminal 300

A120
Acquire
first image sequence

A110
Transmit
first image sequence

A130
Derive second image
sequence

A140
Derive gradient

A150
Normalize gradient

A160
Derive divergence

A170
Derive third image
sequence

A180
Derive fourth image
sequence

A190
Detect occurrence
position and occurrence
time of source
excitation wave

A200
Generate position
information and time
information

A220
Receive position
information and time
information

A210
Transmit position
information and time
information

A230
Display position
information and time
information

410

420

430

440

450

460

470

INFORMATION PROCESSING SYSTEM, PROGRAM, AND INFORMATION PROCESSING METHOD

CROSS REFERENCE TO RELATED APPLICATIONS

This application is a 371 U.S. National Phase of International Application No. PCT/JP2022/045402, filed on Dec. 9, 2022, which claims priority to U.S. Patent Application No. 63/288,009, filed Dec. 10, 2021. The entire disclosures of the above applications are incorporated herein by reference.

BACKGROUND

Technical Field

The present invention relates to an information processing system, a program, and an information processing method.

Background Art

JP2018-171194 A discloses an analysis map creating apparatus.

This analysis map creating apparatus calculates a phase variance value indicating a degree of variance of a phase in a surrounding of each position in a biological tissue, based on phase values of excitation wave at respective positions in the biological tissue that acts in response to excitation caused by propagation of the excitation wave in the tissue, and generates an analysis map, based on a time series of at least part of the phase variance values at the respective positions. Since the phase variance value indicates the degree of variance of the phase in the surrounding, a position having a large degree of variance of the phase in the surrounding may be specified as a rotation center of rotating excitation wave. In addition, the degree of variance of the phase in the surrounding can suggest that the position was a rotation center at a time prior to the present time or suggest that the position is likely to become a rotation center at a time after the present time. As a result, this configuration generates an analysis map used to make an analysis with regard to the rotating excitation wave.

Two types of abnormal excitation are known to occur: rotating excitation waves and source excitation waves. However, the apparatus disclosed in JP2018-171194 A did not correspond to source excitation waves.

In view of the above circumstances, the present invention provides an information processing system configured to detect occurrence positions of source excitation waves.

SUMMARY

According to an aspect of the present invention, an information processing system is provided. This information processing system comprises an acquisition unit; a derivation unit; a detection unit; and a generation unit. The acquisition unit is configured to acquire a first image sequence representing a change in membrane potential in a biological tissue. The derivation unit is configured to derive a second image sequence representing the change in the membrane potential by using a circular variable based on the first image sequence and a first derivation equation. The detection unit is configured to detect an occurrence position of a source excitation wave in the biological tissue based on the second image sequence and a first detection formula. The generation unit is configured to generate position information on the occurrence position.

According to such an aspect, it is possible to detect an occurrence position of the source excitation wave.

BRIEF DESCRIPTION OF THE DRAWINGS

FIG. 5 is an activity diagram showing a flow of information processing executed by the information processing apparatus 200.

DETAILED DESCRIPTION

Hereinafter, an embodiment of the present invention will be described with reference to drawings. Various features described in the embodiment below can be combined with each other.

A program for realizing a software described in the present embodiment may be provided as a non-transitory computer-readable memory medium, may be provided to be downloaded via an external server, or may be provided so that the program is activated on an external computer and the program's function is realized on a client terminal (that is, the function is provided by so-called cloud computing).

A term "unit" in the present embodiment may include, for example, a combination of a hardware resource implemented as circuits in a broad sense and information processing of software that can be concretely realized by the hardware resource. Furthermore, various kinds of information are described in the present embodiment, and such information may be represented by, for example, physical values of signal values representing voltage and current, high and low signal values as a set of binary bits consisting of 0 or 1, or quantum superposition (so-called qubits), and communication and computation may be executed on a circuit in a broad sense.

The circuit in a broad sense is a circuit realized by properly combining at least a circuit, circuitry, a processor, a memory, and the like. In other words, a circuit includes an application specific integrated circuit (ASIC), a programmable logic device (e.g., simple programmable logic device (SPLD), a complex programmable logic device (CLPD), field programmable gate array (FPGA), and the like.

1. Hardware Configuration

Section 1 describes a hardware configuration according to the present embodiment.

1-1. Information Processing System 100

Figure 1:
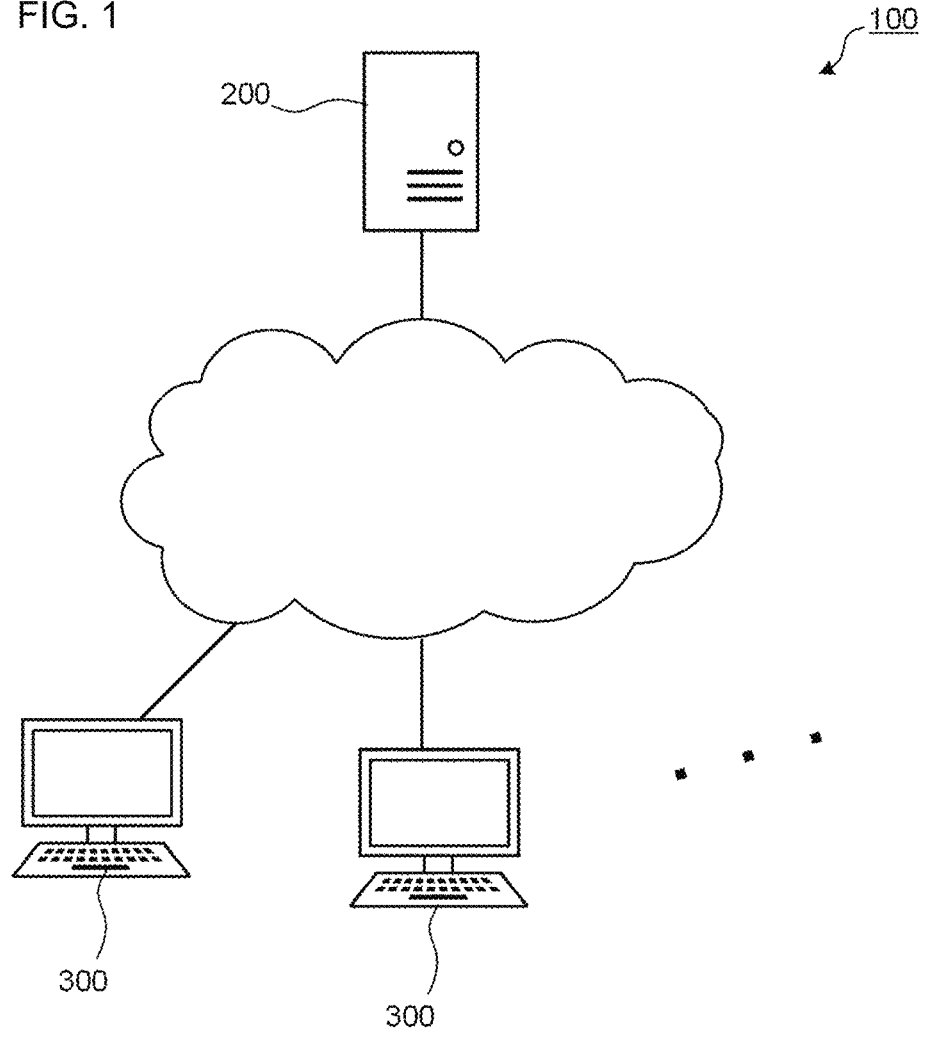
FIG. 1 is a configuration diagram showing an information processing system 100.

FIG. 1 is a configuration diagram showing an information processing system 100. The information processing system 100 comprises an information processing apparatus 200 and a terminal 300, which are connected through a network. These components will be described further. The system exemplified by the information processing system 100 comprises one or more devices or components. Thus, for example, even a single information processing apparatus 200 can be a system exemplified by the information processing system 100.

1-2. Information Processing Apparatus 200

Figure 2:
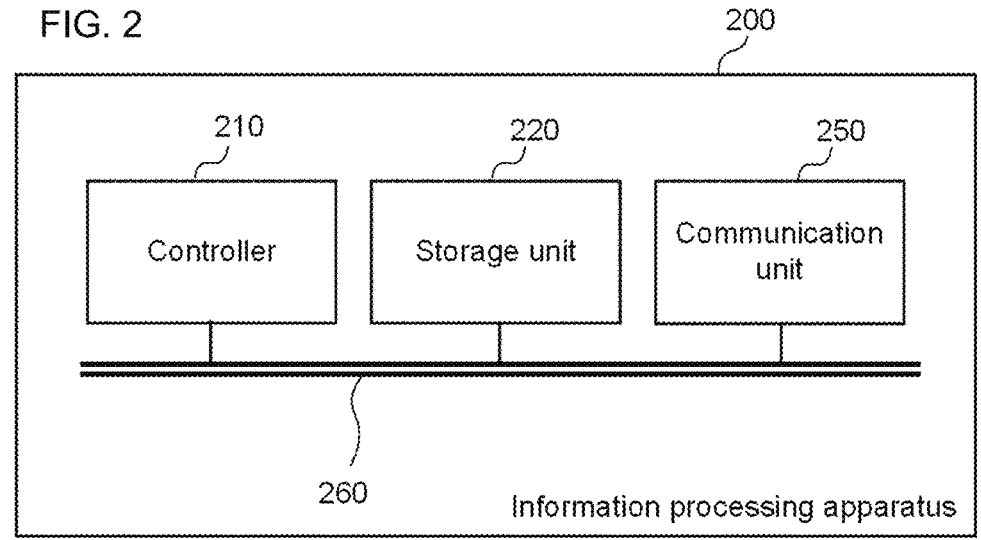
FIG. 2 is a block diagram showing a hardware configuration of an information processing apparatus 200.

FIG. 2 is a block diagram showing a hardware configuration of the information processing apparatus 200. The information processing apparatus 200 comprises a controller 210, a storage unit 220, and a communication unit 250, and these components are electrically connected inside the information processing apparatus 200 via a communication bus 260. The information processing apparatus 200 can function as a server. Each component will be further described.

The controller 210 executes processing and control of overall operation related to the information processing apparatus 200. The controller 210 is, for instance, an unshown CPU (Central Processing Unit). The controller 210 is configured to read a predetermined program stored in the storage unit 220 to realize various functions with respect to the information processing apparatus 200. In other words, information processing by software stored in the storage unit 220 can be executed as each function execution unit included in the controller 210 by specifically realized through the controller 210, that is an example of hardware. These will be described in further detail in Section 2. The controller 210 is not limited to being a single controller but may be implemented with a plurality of controllers 210 for each function. Moreover, a combination thereof may be applied.

The storage unit 220 is configured to store various information necessary for information processing of the information processing apparatus 200. This can be implemented, for example, as a storage device such as an SSD (Solid State Drive) that stores various programs, etc. related to the information processing apparatus 200 executed by the controller 210, or as a memory such as an RAM (Random Access Memory) that stores temporarily necessary information (arguments, sequences, etc.) for calculation of program. Further, a combination thereof may be applied.

Although wired communication method such as USB, IEEE1394, Thunderbolt (registered trademark), wired LAN network communication, etc. are preferred, the communication unit 250 may include wireless LAN network communication, mobile communication such as 5G/LTE/3G, Bluetooth (registered trademark) communication, etc. as necessary. That is, it is further preferable to implement as a set of these communication means. In other words, the information processing apparatus 200 communicates various information with the terminal 300 via the network through the communication unit 250.

1-3. Terminal 300

Figure 3:
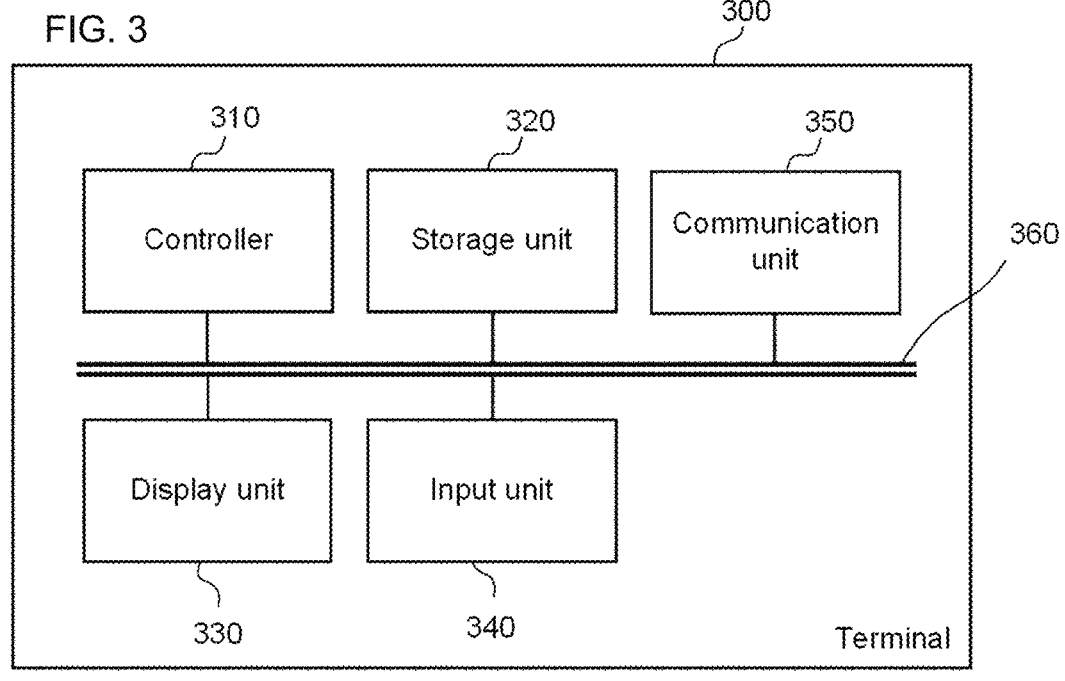
FIG. 3 is a block diagram showing a hardware configuration of a terminal 300.

FIG. 3 is a block diagram showing a hardware configuration of the terminal 300. The terminal 300 comprises a controller 310, a storage unit 320, a display unit 330, an input unit 340, and a communication unit 350, and these components are electrically connected via a communication bus 360 in the terminal 300. Descriptions of the controller 310, the storage unit 320 and the communication unit 350 are omitted since they are substantially the same as those of the controller 210, the storage unit 220 and the communication unit 250 in the information processing device 200.

The display unit 330 may be included in a housing of the terminal 300, or may be externally provided. The display unit 330 displays a graphical user interface (GUI) screen that can be operated by the user. This should be implemented, for example, by using different display devices such as a CRT display, a liquid crystal display, an organic EL display, and a plasma display, depending on the type of the terminal 300. Hereinafter, the display unit 330 is described as to be included in the housing of the terminal 300.

The input unit 340 may be included in the housing of the terminal 300 or may be externally provided. For example, the input unit 340 may be integrated with the display 330 and implemented as a touch panel. With a touch panel, the user can input taps, swipes, etc. Of course, a switch button, mouse, QWERTY keyboard, etc. may be employed instead of a touch panel. In other words, the input unit 340 receives operation inputs made by the user. Said input is transferred as an instruction signal to the controller 310 via the communication bus 360. The controller 310 can perform predetermined control and operations as necessary.

2. Functional Structure

Section 2 describes the functional structure of the present embodiment. As mentioned above, information processing by software stored in the storage unit 220 is specifically realized by the controller 210, which is an example of hardware, and can be executed as each functional unit included in the controller 210.

Figure 4:
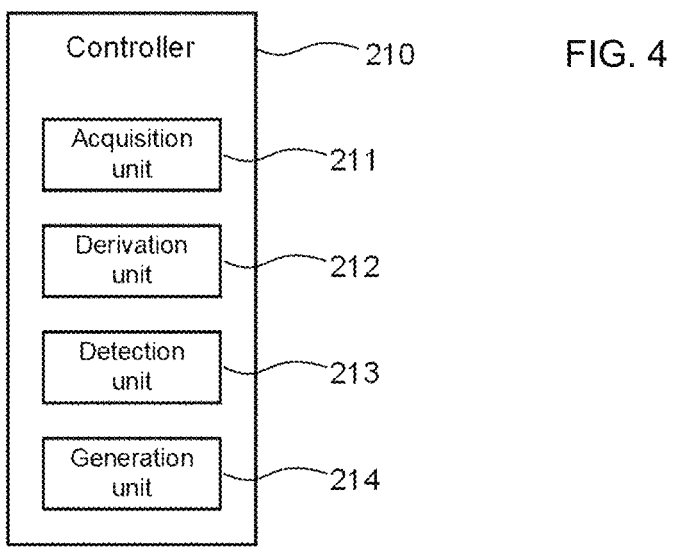
FIG. 4 is a block diagram indicating the functions realized by the information processing apparatus 200 (controller 210).

FIG. 4 is a block diagram indicating functions realized by the information processing apparatus 200 (controller 210). Specifically, the information processing apparatus 200 (controller 210) includes an acquisition unit 211, a derivation unit 212, a detection unit 213, and a generation unit 214.

The acquisition unit 211 is configured to acquire various information. For example, the acquisition unit 211 acquires a first image sequence representing changes in membrane potential in biological tissues from the terminal 300.

The derivation unit 212 is configured to derive various information. For example, the derivation unit 212 derives a second image sequence representing changes in membrane potential by using a circular variable based on the first image sequence and a first derivation equation.

The detection unit 213 is configured to detect various information. For example, the detection unit 213 detects an occurrence position of a source excitation wave in the biological tissue based on the second image sequence and a first detection formula.

The generation unit 214 is configured to generate various information. For example, the generation unit 214 generates position information on the occurrence position of the detected source excitation wave.

3. Information Processing Method

Section 3 describes an information processing method of the information processing apparatus 200 described above. This information processing method is executed by a computer using each part of the information processing apparatus 200 (controller 210) as each step. Specifically, this information processing method includes an acquisition step, a derivation step, a detection steps, and a generation step. In the acquisition step, a first image sequence representing changes in membrane potential in a biological tissue is acquired. In the derivation step, a second image sequence representing changes in membrane potential is derived using a circular variable based on the acquired first image sequence and a first derivation equation. In the detection step, an occurrence position of the source excitation wave in the biological tissue is detected based on the derived second image sequence and a first detection formula. In the generation step, position information on the detected occurrence position of the source excitation wave is generated.

Figure 6:
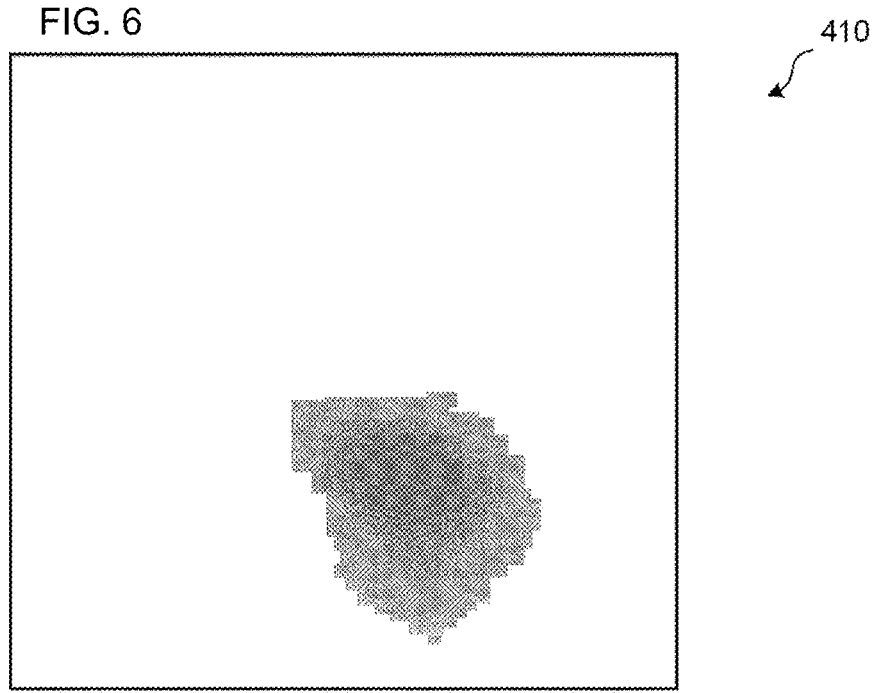
FIG. 6 is an example of an image (a membrane potential image 410) included in the first image sequence.
Figure 7:
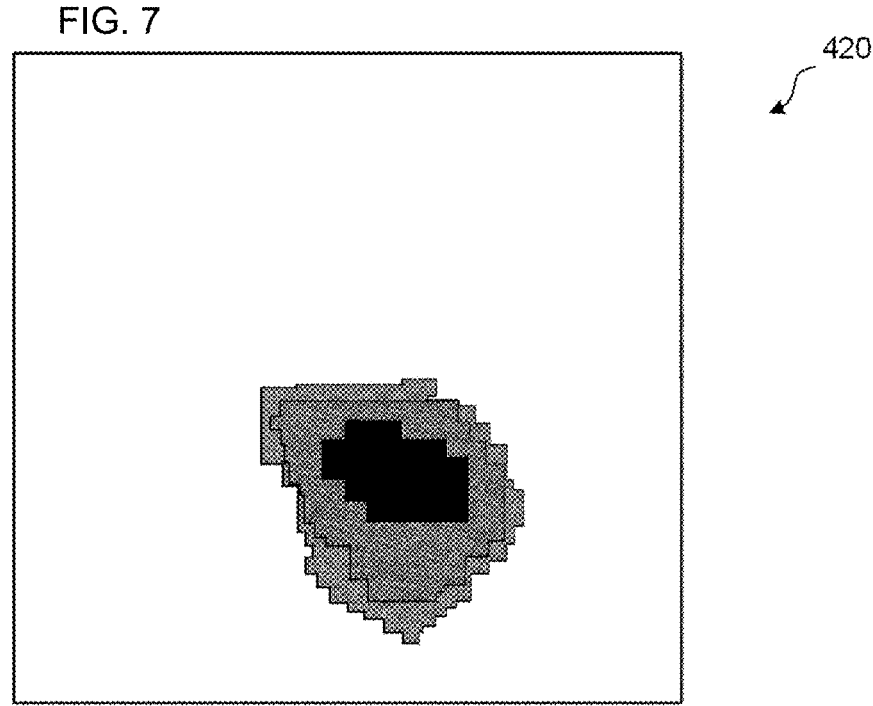
FIG. 7 is an example of an image (a phase map image 420) included in the second image sequence.
Figure 8:
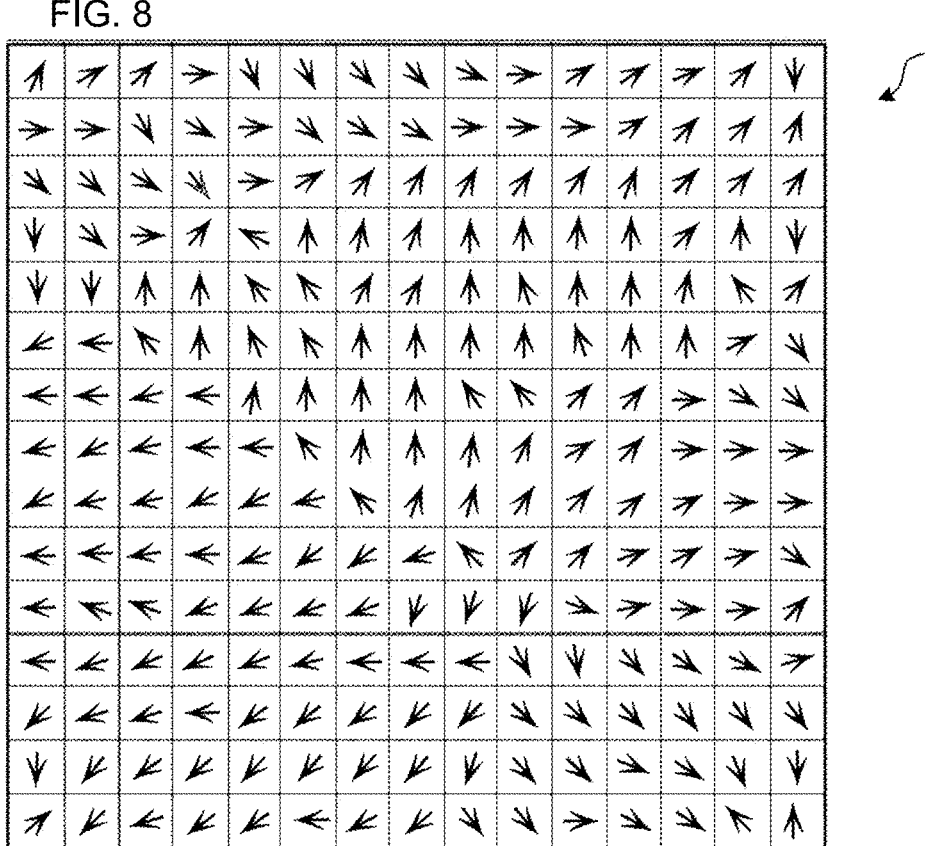
FIG. 8 is an example of gradients of a circular variable (a phase gradient 430) in the phase map image 420.
Figure 9:
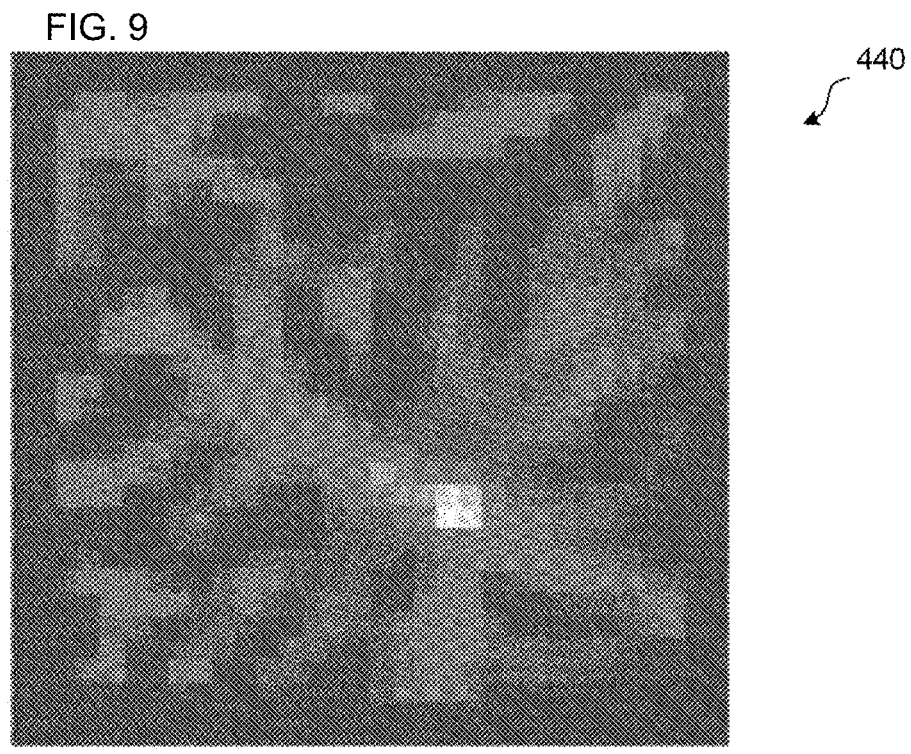
FIG. 9 is an example of an image (a divergence image 440) indicating divergence of the gradient of the circular variable.
Figure 10:
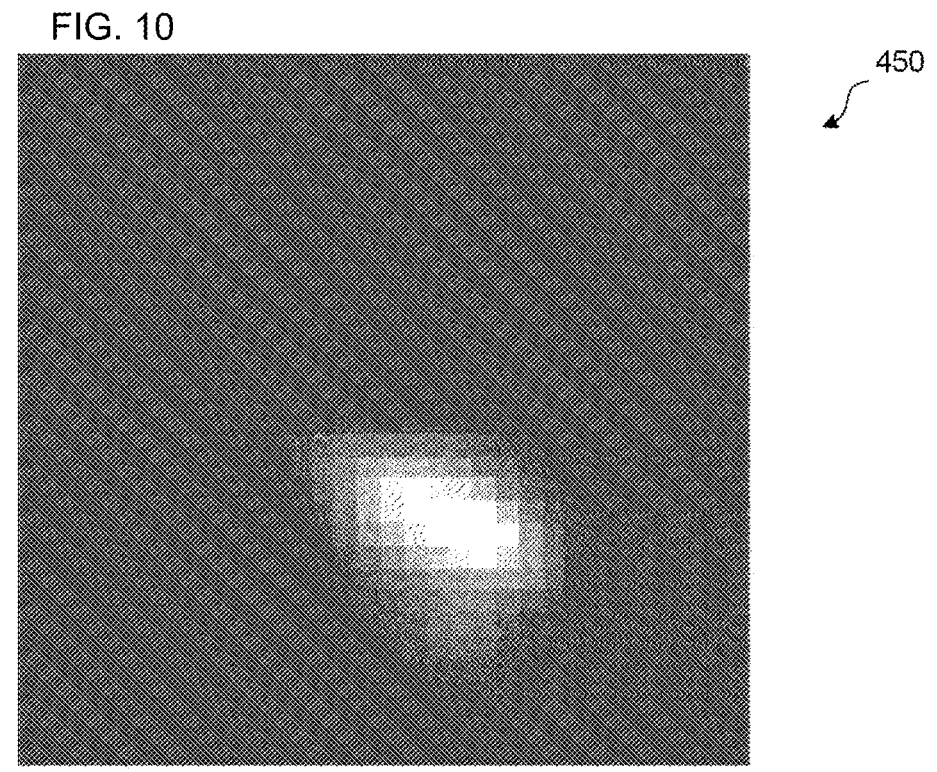
FIG. 10 is an example of an image (a coefficient application image 450) in which the change in the membrane potential in the phase map image 420 has been processed.
Figure 11:
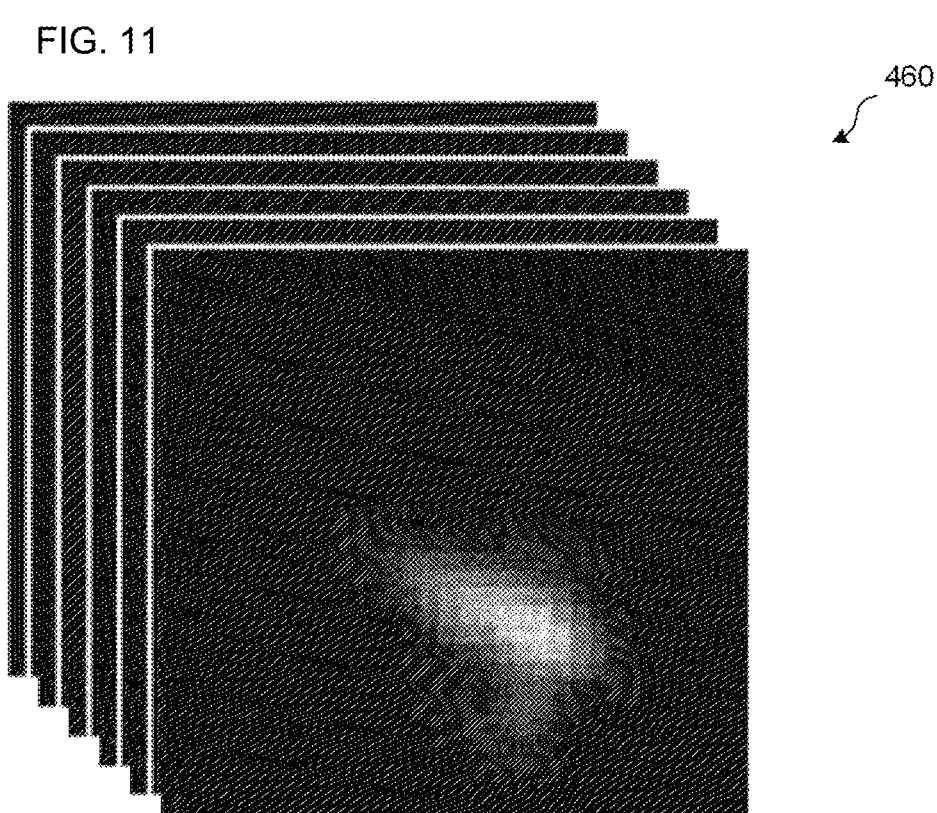
FIG. 11 is a diagram showing a coefficient application image sequence 460 configured of image sequences of coefficient application images 450.
Figure 12:
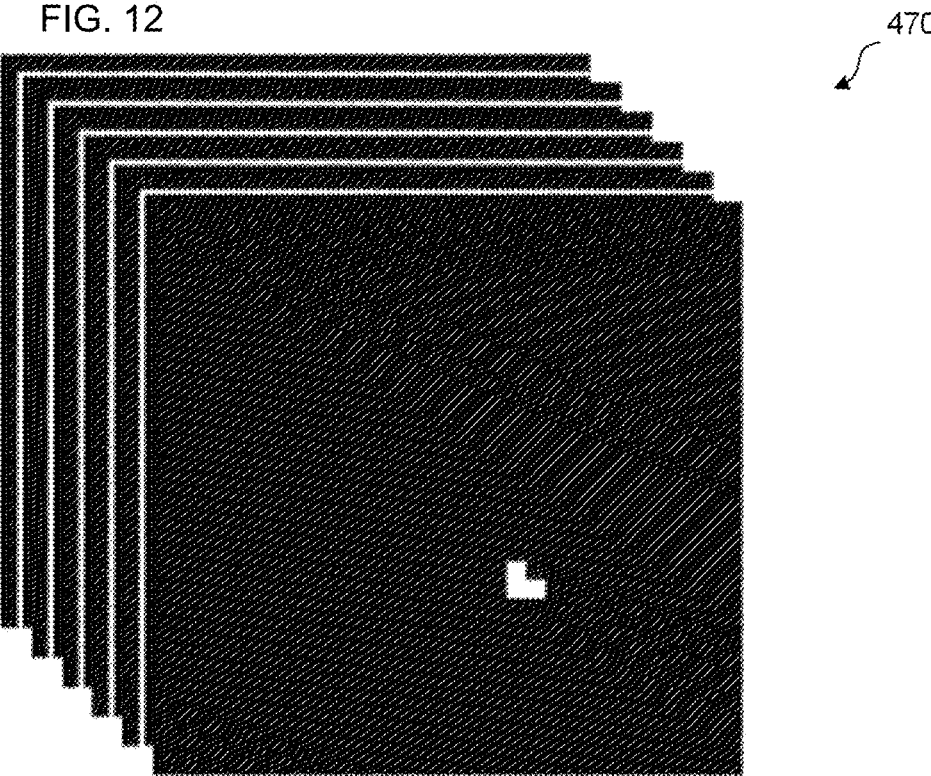
FIG. 12 is a diagram showing a binarized image sequence 470 in which the changes in the membrane potential in the coefficient application image sequence 460 are binarized.
Figure 13:
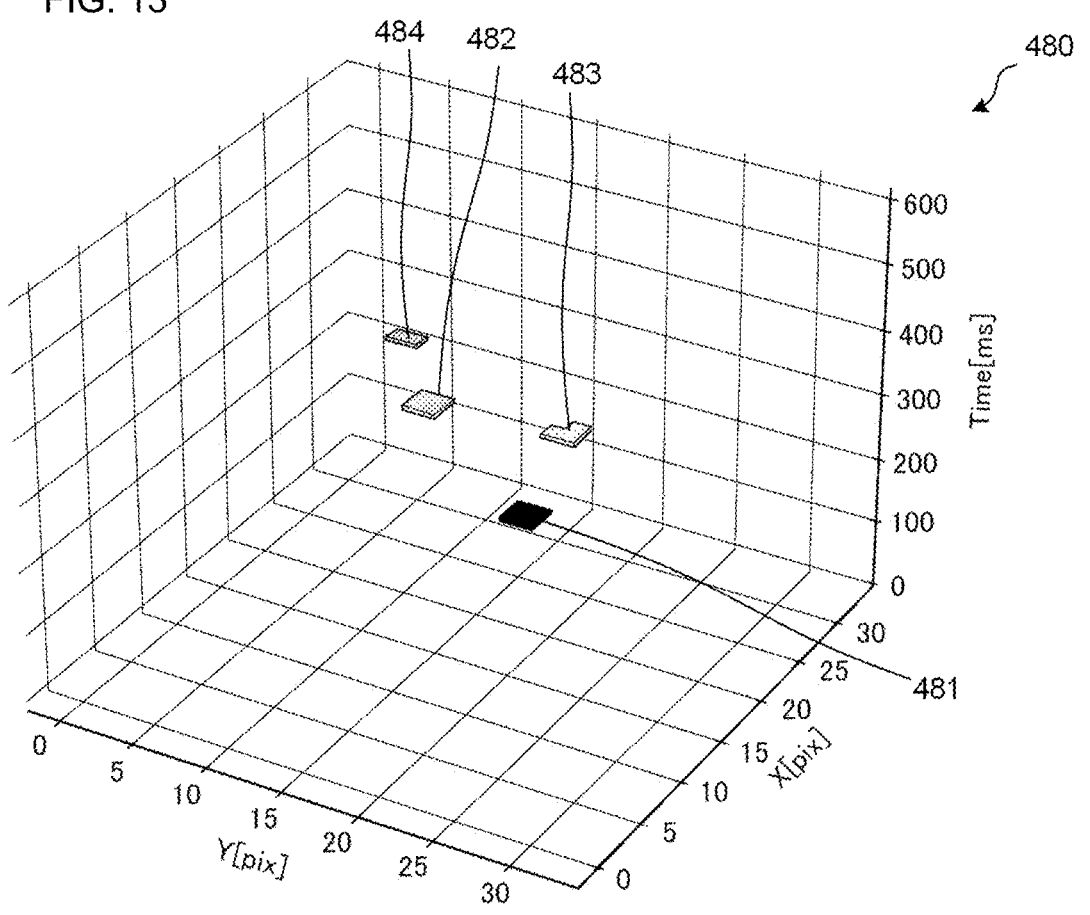
FIG. 13 is a diagram showing results of labeling position information on the occurrence position of the source excitation wave in the biological tissue and labeling time information on the occurrence time of the source excitation wave.

FIG. 5 is an activity diagram showing a flow of information processing executed by the information processing apparatus 200. The explanation will be given according to each activity in this activity diagram. FIG. 6 shows an example of an image (a membrane potential image 410) included in the first image sequence. FIG. 7 shows an example of an image (a phase map image 420) included in the second image sequence. FIG. 8 shows an example of gradients of a circular variable (a phase gradient 430) in the phase map image 420. FIG. 9 shows an example of an image (a divergence image 440) indicating divergence of the gradient of the circular variable. FIG. 10 shows an example of an image (a coefficient application image 450) in which the change in the membrane potential in the phase map image 420 has been processed. FIG. 11 shows a coefficient application image sequence 460 configured of image sequences of the coefficient application image 450. FIG. 12 shows a binarized image sequence 470 in which the changes in the membrane potential in the coefficient application image sequence 460 are binarized. FIG. 13 shows results of labeling position information on the occurrence position of the source excitation wave in the biological tissue and labeling time information on the occurrence time of the source excitation wave.

Here, the terminal 300 is assumed to store the first image sequence (an image sequence configured of a plurality of the membrane potential images 410) acquired from an unshown high-speed camera. The first image sequence is an image sequence representing changes in membrane potential in a biological tissue. The biological tissue is assumed to be the heart. Furthermore, the circular variable is assumed to be a phase.

The controller 310 in the terminal 300 transmits an image sequence (hereinafter also referred to as "a membrane potential image sequence") configured of a plurality of membrane potential images 410 representing changes in membrane potential in the heart (Activity A110). The membrane potential image sequence corresponds to the first image sequence in the claims. In Activity A110, for example, the following two steps of information processing are executed. (1) The controller 310 reads the membrane potential image sequence stored in the storage unit 320. (2) The controller 310 transmits the membrane potential image sequence to the information processing apparatus 200 via the communication unit 350.

The controller 210 in the information processing apparatus 200 then acquires the membrane potential image sequence from the terminal 300 (Activity A120). In other words, the acquisition unit 211 acquires a first image sequence representing changes in the membrane potential in the biological tissues. In Activity A120, for example, the following two steps of information processing are executed. (1) The communication unit 250 receives the membrane potential image sequence transmitted from the terminal 300. (2) The controller 210 allows the storage unit 220 to store the received membrane potential image sequence.

The controller 210 in the information processing apparatus 200 then derives an image sequence (hereinafter also referred to as "phase map image sequence") configured of a plurality of phase map images 420 representing changes in the membrane potential in the heart using the phase (Activity A130). The phase map image sequence corresponds to the second image sequence in the claims. The phase map image sequence is derived, for example, by performing Hilbert transform on the membrane potential image sequence (corresponding to the first derivation equation in the claims). In other words, the derivation unit 212 derives a second image sequence representing changes in membrane potential in the biological tissues by using a circular variable based on the first image sequence and the first derivation equation. In activity A130, for example, the following three steps of information processing are executed. (1) The controller 210 reads the membrane potential image sequence stored in the storage unit 220 and a program related to the Hilbert transform. (2) The Controller 210 executes derivation processing and derives a phase map image sequence. (3) The controller 210 allows the storage unit 220 to store the derived phase map image sequence.

Here, Equation (1) related to the Hilbert transform is shown as an example of the first derivation equation.

[Equation 1]

$$H[V](t) = \frac{1}{\pi}\int_{-\infty}^{\infty}\frac{V(\tau)}{t-\tau}d\tau \tag{1}$$

The controller 210 in the information processing apparatus 200 then derives the phase gradient 430 for each phase map image 420 (Activity A140). The phase gradient 430 is derived, for example, by partially differentiating and vectorizing each phase map image 420 (corresponding to the second derivation equation in the claims). In other words, the derivation unit 212 derives gradients of the circular variable based on the second image sequence and the second derivation equation. In Activity A140, for example, the following three steps of information processing are executed. (1) The controller 210 reads the second image sequence stored in the storage unit 220 and a program regarding a gradient (e.g., a program that executes partial differentiation and vectorization). (2) The controller 210 executes the derivation processing and derives the phase gradient 430 for each phase map image 420. (3) The controller 210 allows the storage unit 220 to store the derived phase gradients 430.

The controller 210 in the information processing apparatus 200 then normalizes each phase gradient 430 (Activity A150). The normalization is executed, for example, by multiplying an inverse number of the phase gradient 430 to the phase gradient 430 (corresponding to the third derivation equation in the claims). In other words, the derivation unit 212 normalizes the gradient of the circular variable based on the gradient of the circular variable and the third derivation equation. In Activity A150, for example, the following three steps of information processing are executed. (1) The controller 210 reads the phase gradient 430 stored in the storage unit 220 and a program related to the normalization (e.g., a program that obtains an inverse number of the phase gradient 430 and processes the phase gradient 430 with this inverse number). (2) The controller 210 executes a normalization process to normalize each phase gradient 430. (3) The controller 210 allows the storage unit 220 to store each normalized phase gradient 430.

The controller 210 in the information processing apparatus 200 then derives a divergence image 440 for each normalized phase gradient 430 (Activity A160). The divergence image 440 is derived, for example, by adding a value obtained by partially differentiating each component of the vector field in each normalized phase gradient 430, in its axial direction (corresponding to the fourth derivation equation in the claims). In other words, the derivation unit 212 derives the divergence of the gradient of the circular variable based on the gradient of the circular variable and the fourth derivation equation. In activity A160, for example, the following three steps of information processing are executed. (1) The controller 210 reads the normalized phase gradient 430 stored in the storage unit 220 and a program related to the divergence (e.g., a program that adds a value obtained by partially differentiating each component of the vector field in its axial direction). (2) The controller 210 executes the derivation process and derives a divergence image 440 for the normalized phase gradient 430. (3) The controller 210 allows the storage unit 220 to store each derived divergence image 440.

Here, Equation 2 related to divergence is shown as an example of the fourth derivation equation.

[Equation 2]

$$\text{Divergence} = \frac{\partial G_x}{\partial x} + \frac{\partial G_y}{\partial y} \quad (2)$$

G: Phase Gradient after Normalization

The controller 210 in the information processing apparatus 200 then derives an image sequence (hereinafter also referred to as a "coefficient application image sequence 460") configured of a plurality of coefficient application images 450 for each divergence image 440. (Activity A170). The coefficient application image sequence 460 is an image sequence in which the changes in the membrane potential in the phase map image sequence are processed. The coefficient application image sequence 460 corresponds to the third image sequence in the claims. In other words, the derivation unit 212 derives the third image sequence in which the changes in the membrane potential in the second image sequence are processed based on the divergence of the gradient of the circular variable and a predetermined coefficient. This coefficient is a coefficient that focuses only on the front of the source excitation wave. In Activity A170, for example, the following three steps of information processing are executed. (1) The controller 210 reads a plurality of divergence images 440 stored in the storage unit 220 and the predetermined coefficient. (2) The controller 210 executes a derivation process to derive a coefficient application image sequence 460. (4) The controller 210 allows the storage unit 220 to store the derived coefficient application image sequence 460.

Here, Equations (3) and (4) related to the predetermined coefficients are shown.

[Equation 3]

$$IPC = \exp\left(-\frac{(\theta - \theta_{act})^2}{2\sigma^2}\right) \quad (3)$$

$$\text{Proposed index} = -\frac{1}{2}IPC\left(\frac{\partial G_x}{\partial x} + \frac{\partial G_y}{\partial y}\right) \quad (4)$$

θ: Phase, G: Phase gradient after normalization,
$\theta_{act}$: Phase corresponding to passage time of excitation wave The controller 210 in the information processing apparatus 200 then derives a binarized image sequence 470 from the coefficient application image sequence 460 (Activity A180). The binarized image sequence 470 is derived, for example, by setting a threshold value to an arbitrary value (e.g., 0.8) and executing a binarization process based on the threshold value (corresponding to the fifth derivation equation in the claims). The binarized image sequence 470 corresponds to the fourth image sequence in the claims. In other words, the derivation unit 212 derives the fourth image sequence in which the changes in the membrane potential in the third image sequence are binarized based on the third image sequence and the fifth derivation equation. The threshold values are specifically, for example, 0.1, 0.2, 0.3, 0.4, 0.5, 0.6, 0.7, 0.8, 0.9, or 1.0, and may be in the range between any two of the values shown above. In Activity A180, for example, the following three steps of information processing are executed. (1) The controller 210 reads the coefficient application image sequence 460 stored in the storage unit 220 and a program related to the binarization process. (2) The controller 210 executes the derivation processing and derives a binarized image sequence 470. (3) The controller 210 allows the storage unit 220 to store the derived binarized image sequence 470.

The controller 210 in the information processing apparatus 200 then detects an occurrence position and an occurrence time of the source excitation wave in the heart (activity A190). The occurrence position and the occurrence time of the source excitation wave are detected, for example, by labeling the portion corresponding to the front of the excitation wave in the binarized image sequence 470 and based on the center of gravity in the spatiotemporal direction of this labeled portion (corresponding to the third detection formula in the claims). In other words, the detection unit 213 detects an occurrence position and an occurrence time of a source excitation wave in the biological tissue based on the fourth image sequence and the third detection formula. In Activity A 190, for example, the following three steps of information processing are executed. (1) The controller 210 reads the binarized image sequence 470 and the third detection formula stored in the storage unit 220. (2) The controller 210 executes a detection processing and detects an occurrence position and an occurrence time of the source excitation wave. (3) The controller 210 allows the storage unit 220 to store the information on the occurrence position and the occurrence time of the detected source excitation wave.

The controller 210 in the information processing apparatus 200 then generates a labeling image 480, which indicates position information on the occurrence position and time information on the occurrence time of the source excitation wave in the heart (Activity A200). In other words, the generation unit 214 generates position information on the occurrence position of the source excitation wave in the biological tissues and time information on the occurrence time of the source excitation wave in the biological tissues. In Activity A200, for example, the following three steps of information processing are executed. (1) The controller 210 reads the information on the occurrence position and the occurrence time of the source excitation wave stored in the storage unit 220. (2) The controller 210 executes generation processing and generates a labeling image 480. (3) The controller 210 allows the storage unit 220 to store the labeling image 480.

The controller 210 in the information processing apparatus 200 then transmits the labeling image 480 to the terminal 300 (Activity A210). In Activity A210, for example, the following two steps of information processing are executed. (1) The controller 210 reads the labeling image 480 stored in storage unit 220. (2) The controller 210 transmits the labeling image 480 to the terminal 300 via the communication unit 250.

The controller 310 in the terminal 300 then receives the labeling image 480 from the information processing apparatus 200 (Activity A220). In Activity A220, for example, the following two steps of information processing are executed. (1) The communication unit 350 receives the labeling image 480 transmitted from the information processing apparatus 200. (2) The controller 310 allows the storage unit 320 to store the received labeling image 480.

The controller 310 in the terminal 300 then allows the display unit 330 to display the labeling image 480 (Activity A230). In Activity A230, for example, the following two steps of information processing are executed. (1) The controller 310 reads the labeling image 480 stored in the storage unit 320. (2) The controller 310 executes display processing and allows the display unit 330 to display the labeling image 480.

In the labeling image 480, label 481, label 482, label 483 and label 484 are drawn. The labels 481, 482, 483 and 484 correspond to the occurrence positions and the occurrence time of the source excitation wave in the heart. In other words, when an arbitrary position is set as the origin and when counting from 0 seconds, it is possible to recognize the occurrence of a source excitation wave in the following order (1) to (4). (1) First, a source excitation wave occurred at a position of 32 pixels by 12 pixels (label 481). (2) Then, 100 milliseconds after (1), a source excitation wave occurred at a position of 33 pixels by 3 pixels (label 482). (3) Then, 10 milliseconds after (2), a source excitation wave occurred at a position of 34 pixels by 13 pixels (label 483). (4) Then, 80 milliseconds after (3), a source excitation wave occurred at a position of 35 pixels by 2 pixels (label 484).

4. Experimental Example

Section 4 describes an experimental example of the present embodiment.

4-1. Experimental Conditions

First, an atrioventricular block was prepared from an excised porcine heart, and a Langendorff-perfused porcine heart specimen was prepared. The perfused heart specimen was then stained with a membrane potential sensitive dye (Di-4-ANNEPS from Thermo Fisher Scientific), and a muscle contraction inhibitor (2,3-butanedionemonoxime from Sigma-Aldrich) was added to the perfusate to remove motion artifacts. Water column pressure was then applied in the atrium of the perfused heart specimen to induce ventricular fibrillation in the perfused heart specimen. Then, electrical stimulation was applied to the perfused heart specimen using a stimulator (SEC-5104 from Nihon Kohden).

Then, the perfused heart specimen was irradiated with 520 nm excitation light from a ring light in which two hundred high-intensity blue-green LEDs (Xeom 3 Power Pure Green LEDs from Opto supply) were arranged in a ring shape. The generated emitted fluorescence was then photographed through a peephole in the center of the ring light by a high-speed camera (Mini-AX50 from Photron) through a long-pass filter with a cutoff wavelength of 600 nm at 1000 fps and 512 pixels×512 pixels. The photographed image sequence was then imported into the terminal 300.

4-2. Examples

In the example, the processing in the present embodiment was executed. That is, the image sequence imported into the terminal 300 was processed by the information processing apparatus 200 (Activities A120 to A210), and the generated labeling image 480 was displayed on the terminal 300 to confirm the occurrence position and the occurrence time of the source excitation wave.

4-3. Comparative Examples

In the comparison examples, processing in the existing method was executed. That is, the image sequence imported into the terminal 300 was processed as follows. First, an activation map was created by calculating passage time of the source excitation wave and mapping the time until the next excitation. Then, based on the created activation map, the gradients were calculated from Equations (5) and (6), respectively. Equations (5) and (6) were then substituted into Equation (7) to calculate a conduction velocity of the excitation wave. Then, Equation (7) was substituted into Equation (8) to derive the divergence of the activation map. The region having high divergence was then detected as a source excitation wave, and the occurrence position and the occurrence time of the source excitation wave were confirmed.

[Equation 4]

$$G_x = \frac{\partial \mathrm{Act}}{\partial x} [\mathrm{ms}/pix] \tag{5}$$

$$G_y = \frac{\partial \mathrm{Act}}{\partial y} [\mathrm{ms}/pix] \tag{6}$$

$$v = \left( \frac{G_x}{G_x^2 + G_y^2}, \frac{G_y}{G_x^2 + G_y^2} \right) [pix/\mathrm{ms}] \tag{7}$$

Act: Pixel value of activation map

[Equation 5]

$$\mathrm{Divergence} = \frac{\partial v_x}{\partial x} + \frac{\partial v_y}{\partial y} \tag{8}$$

V: Excitation conduction velocity vector after normalization

4-4. Evaluation Method

A correct answer was determined by visually determining the occurrence position of the source excitation wave from the image sequence imported into the terminal 300, and by determining the passage time when passing the front of the source excitation wave as an occurrence time of the source excitation wave. The first condition was that the difference in distance among the occurrence position of the correct answer, the occurrence position in the example and the occurrence position in the comparative example should be within four pixels. In addition, the second condition was that the difference in interval between the occurrence time of the correct answer and the occurrence time of the example should be within ten milliseconds. When the first and second conditions were satisfied in each of the example and comparative example, the detection of the source excitation wave was considered successful.

4-5. Evaluation Results

In following Tables 1 and 2, "Positive" indicates the occurrence of source excitation waves, and "Negative" indicates no source excitation waves.

TABLE 1

| Example | | Detection results | |
|---|---|---|---|
| | | Positive | Negative |
| Correct value | Positive | 69 | 20 |
| | Negative | 77 | — |

TABLE 2

| Comparison example | | Detection results | |
|---|---|---|---|
| | | Positive | Negative |
| Correct value | Positive | 71 | 18 |
| | Negative | 4973 | — |

4-6. Conclusion

The Example showed that the false positives in the comparative example (i.e., Positive was detected when the correct value was Negative) was able to be suppressed. In other words, it was shown that the Example was superior to the comparative example using the existing method.

Although the embodiments of the present invention have been described above, the present invention is not limited thereto and can be modified as appropriate without departing from the technical concept of the present invention.

5. Modified Examples

Section 5 describes a modified example of the present embodiment.

An aspect of the present invention may be a program. The program allows a computer to function as each unit of the information processing apparatus 200.

The controller 210 executes a writing (memory) process and a reading process on various types of data and various types of information into and from the storage unit 220, but processes are not limited to these, and the controller 210 may use, for example, a register or a cache memory in the controller 210 to execute information processing for each activity.

The detection unit 213 has been described as detecting the occurrence position and the occurrence time of the source excitation wave based on the fourth image sequence and the third detection formula, but the configuration is not limited thereto. For example, the detection unit 213 may detect the occurrence position and the occurrence time of the source excitation wave based on the third image sequence and the second detection formula. At this time, for example, the second detection formula may be a formula that labels the portion corresponding to the front of the excitation wave in the coefficient application image sequence 460 and performs a detection based on the center of gravity in the spatiotemporal direction of this labeled portion.

The detection unit 213 has been described as detecting the occurrence position and the occurrence time of the source excitation wave, but the configuration is not limited thereto. The detection unit 213 may be one that detects the occurrence position of the source excitation wave. Thus, for example, the detection unit 213 may detect the occurrence position of the source excitation wave in the biological tissue based on the second image sequence and the first detection formula. At this time, the first detection formula may be, for example, a formula that labels the portion corresponding to the front of the excitation wave in the phase map image sequence and performs a detection based on the center of gravity in the spatiotemporal direction of this labeled portion.

The generation unit 214 has been described as generating position information on the occurrence position and time information on the occurrence time, but the configuration is not limited thereto. The generation unit 214 may be one that generates position information on the occurrence position of the source excitation wave. Thus, for example, the generation unit 214 may generate position information on the occurrence position of the source excitation wave.

The biological tissue has been described as the heart, but the biological tissue is not limited thereto. The biological tissue may be, for example, a nerve.

6. Others

The present invention may be provided in each of the following aspects.

(1) An information processing system, comprising: an acquisition unit configured to acquire a first image sequence representing a change in membrane potential in a biological tissue; a derivation unit configured to derive a second image sequence representing the change in the membrane potential by using a circular variable based on the first image sequence and a first derivation equation; a detection unit configured to detect an occurrence position of a source excitation wave in the biological tissue based on the second image sequence and a first detection formula; and a generation unit configured to generate position information on the occurrence position.

According to such an aspect, false positives, which have been a problem in existing methods for detecting source excitation waves, can be suppressed. When the number of false positives is large, the possibility of ablating normal tissue increases. In other words, according to such an aspect, quantitative detection of the source excitation wave is possible while suppressing false positives, thereby preventing damage to normal tissues.

(2) The information processing system according to (1), wherein: the derivation unit derives a gradient of the circular variable based on the second image sequence and a second derivation equation.

According to such an aspect, the influence of temporal constancy on gradients, which has been a problem in existing methods for detecting source excitation waves, can be suppressed. Thus, it is possible to quantitatively detect source excitation waves.

(3) The information processing system according to (2), wherein: the derivation unit normalizes the gradient based on the gradient and a third derivation equation.

According to such an aspect, data on gradients can be arranged in an easy-to-handle format for quantitative detection of source excitation waves.

(4) The information processing system according to (2) or (3), wherein: the derivation unit derives divergence of the gradient based on the gradient and a fourth derivation equation.

According to such an aspect, it is possible to derive the data necessary for quantitative detection of source excitation waves.

(5) The information processing system according to (4), wherein: the derivation unit derives a third image sequence in which the change in the membrane potential in the second image sequence has been processed based on the divergence and a predetermined coefficient, the coefficient is a coefficient that focuses on a front of the source excitation wave, the detection unit detects an occurrence position and an occurrence time of the source excitation wave based on the third image sequence and a second detection formula, and the generation unit generates position information on the occurrence position and time information on the occurrence time.

According to such an aspect, the occurrence time of the source excitation wave can be further detected without the influence of constancy on gradients by reacting only during the time zone when the source excitation wave has occurred.

(6) The information processing system according to (5), wherein: the derivation unit derives a fourth image sequence in which the change in the membrane potential in the third image sequence is binarized, based on the third image sequence and a fifth derivation equation, the detection unit detects an occurrence position and an occurrence time of the source excitation wave based on the fourth image sequence and a third detection formula, and the generation unit generates position information on the occurrence position and time information on the occurrence time.

According to such an aspect, the occurrence position and the occurrence time of the source excitation wave can be detected with high accuracy.

(7) The information processing system according to any one of (1) to (6), wherein: the biological tissue is a heart or a nerve.

According to such an aspect, the source excitation wave can be quantitatively detected in the heart or nerves.

(8) The information processing system according to any one of (1) to (7), wherein: the circular variable is a phase.

According to such an aspect, it is possible to quantitatively detect the source excitation wave with a simple configuration.

(9) A non-transitory computer readable medium storing a program, the program allowing a computer to function as each unit of the information processing system according to any one of claims 1 to 8.

According to such an aspect, false positives, which have been a problem in existing methods for detecting source excitation waves, can be suppressed. When the number of false positives is large, the possibility of ablating normal tissue increases. In other words, according to such an aspect, quantitative detection of the source excitation wave is possible while suppressing false positives, thereby preventing damage to normal tissues.

(10) An information processing method executed by a computer using each unit of the information processing system according to any one of claims 1 to 8 as each step.

According to such an aspect, false positives, which have been a problem in existing methods for detecting source excitation waves, can be suppressed. When the number of false positives is large, the possibility of ablating normal tissue increases. In other words, according to such an aspect, quantitative detection of the source excitation wave is possible while suppressing false positives, thereby preventing damage to normal tissues. It is needless to say that the present invention is not limited to the above.

The invention claimed is:

1. An information processing system, comprising a processor configured to execute a program so as to function as:
an acquisition unit configured to acquire a first image sequence representing a change in membrane potential in a biological tissue;
a derivation unit configured to derive a second image sequence representing the change in the membrane potential by using a circular variable based on the first image sequence and a first derivation equation;
a detection unit configured to detect an occurrence position of a source excitation wave in the biological tissue based on the second image sequence and a first detection formula; and
a generation unit configured to generate position information on the occurrence position.

2. The information processing system according to claim 1, wherein:
the derivation unit derives a gradient of the circular variable based on the second image sequence and a second derivation equation.

3. The information processing system according to claim 2, wherein:
the derivation unit normalizes the gradient based on the gradient and a third derivation equation.

4. The information processing system according to claim 2, wherein:
the derivation unit derives divergence of the gradient based on the gradient and a fourth derivation equation.

5. The information processing system according to claim 4, wherein:
the derivation unit derives a third image sequence in which the change in the membrane potential in the second image sequence has been processed based on the divergence and a predetermined coefficient,
the coefficient is a coefficient that focuses on a front of the source excitation wave,
the detection unit detects an occurrence position and an occurrence time of the source excitation wave based on the third image sequence and a second detection formula, and the generation unit generates position information on the occurrence position and time information on the occurrence time.

6. The information processing system according to claim 5, wherein:

the derivation unit derives a fourth image sequence in which the change in the membrane potential in the third image sequence is binarized, based on the third image sequence and a fifth derivation equation, the detection unit detects an occurrence position and an occurrence time of the source excitation wave based on the fourth image sequence and a third detection formula, and the generation unit generates position information on the occurrence position and time information on the occurrence time.

7. The information processing system according to claim 1, wherein:

the biological tissue is a heart or a nerve.

8. The information processing system according to claim 1, wherein:

the circular variable is a phase.

9. A non-transitory computer readable medium storing a program configured to allow a computer to function as each unit of the information processing system according to claim 1.

10. An information processing method executed by a computer using each unit of the information processing system according to claim 1 as each step.

\* \* \* \* \*